(12) United States Patent
Huang (10) Patent No.: US 10,491,838 B2
(45) Date of Patent: Nov. 26, 2019

(54) IMAGING DEVICE AND PORTABLE MULTISPECTRAL IMAGING AND DISPLAY APPARATUS THEREOF

(71) Applicant: EXPANTRUM OPTOELECTRONICS, Shanghai (CN)

(72) Inventor: Zhongshou Huang, Shanghai (CN)

( * ) Notice: Subject to any disclaimer, the term of this patent is extended or adjusted under 35 U.S.C. 154(b) by 164 days.

(21) Appl. No.: 15/869,846

(22) Filed: Jan. 12, 2018

(65) Prior Publication Data

US 2018/0288341 A1   Oct. 4, 2018

(30) Foreign Application Priority Data

Mar. 30, 2017   (CN) .......................... 2017 1 0202019
Mar. 30, 2017   (CN) .......................... 2017 1 0202248

(51) Int. Cl.
*H04N 5/33*     (2006.01)
*H04N 5/225*    (2006.01)
(Continued)

(52) U.S. Cl.
CPC ........... *H04N 5/332* (2013.01); *A61B 5/0035* (2013.01); *A61B 5/0075* (2013.01); *A61B 5/0077* (2013.01); *A61B 5/1032* (2013.01); *A61B 5/489* (2013.01); *A61B 5/742* (2013.01); *A61B 5/7425* (2013.01); *A61B 6/5247* (2013.01); *G02B 5/208* (2013.01); *H01L 27/1462* (2013.01); *H01L 27/14625* (2013.01); *H01L 27/14627* (2013.01); *H01L 27/14634* (2013.01); *H01L 27/14645* (2013.01); *H01L 27/14649* (2013.01);
(Continued)

(58) Field of Classification Search
CPC .......... A61B 5/0075; A61B 2560/0431; A61B 5/0035; A61B 5/0077; A61B 5/489; A61B 5/6833; A61B 5/742; A61B 5/7425; A61B 6/5247; A61B 2562/02; A61B 2562/0238; A61B 2562/046; A61B 2562/146; A61B 5/0059; A61B 5/0064; A61B 5/1032; H04N 5/332; H04N 5/2254; H04N 5/2256; H04N 5/2258; H04N 5/23293; H04N 5/369; H04N 5/374; H04N 9/045; H04N 9/09; G02B 5/208; G02B 27/286; H01L 27/1462; H01L 27/14625; H01L 27/14627; H01L 27/14634; H01L 27/14645; H01L 27/14649
See application file for complete search history.

(56) References Cited

U.S. PATENT DOCUMENTS

2015/0185152 A1*  7/2015  Maher ................ G01N 21/6452
                                                      506/39

* cited by examiner

*Primary Examiner* — Anner N Holder (57) ABSTRACT

A portable multispectral imaging and display apparatus includes an imaging device and a display device. The imaging device includes a first image sensor configured to obtain image information of light radiation, came through the lens module, of a first spectral range, a second image sensor configured to obtain image information of light radiation, came through the first image sensor, of the second spectral range, the lens module configured to focus the image information of the light radiation of the first spectral range on the first image sensor, and focus the image information of the light radiation of the second spectral range on the second image sensor. The display device is configured to show the image information of the light radiation of the first spectral range and the image information of the light radiation of the second spectral range.

17 Claims, 9 Drawing Sheets

(51) Int. Cl.
*H04N 5/369* (2011.01)
*H04N 5/232* (2006.01)
*H04N 5/374* (2011.01)
*H04N 9/04* (2006.01)
*H04N 9/09* (2006.01)
*H01L 27/146* (2006.01)
*A61B 5/00* (2006.01)
*A61B 5/103* (2006.01)
*A61B 6/00* (2006.01)
*G02B 5/20* (2006.01)
*G02B 27/28* (2006.01)

(52) U.S. Cl.
CPC ......... *H04N 5/2254* (2013.01); *H04N 5/2256* (2013.01); *H04N 5/2258* (2013.01); *H04N 5/23293* (2013.01); *H04N 5/369* (2013.01); *A61B 5/6833* (2013.01); *A61B 2560/0431* (2013.01); *A61B 2562/0238* (2013.01); *A61B 2562/046* (2013.01); *A61B 2562/146* (2013.01); *G02B 27/286* (2013.01); *H04N 5/374* (2013.01); *H04N 9/045* (2013.01); *H04N 9/09* (2013.01)

IMAGING DEVICE AND PORTABLE MULTISPECTRAL IMAGING AND DISPLAY APPARATUS THEREOF

CROSS-REFERENCE

This application is based upon and claims the benefit of priority of Chinese Patent Applications No. 201710202248.X, filed on Mar. 30, 2017 and No. 201710202019.8, filed on Mar. 30, 2017, the entire contents of which are incorporated herein by reference.

TECHNICAL FIELD

The present disclosure relates to the field of multispectral imaging obtaining device, and more particularly, to an imaging device for obtaining infrared images and visible light images, and a portable multispectral imaging and displaying apparatus thereof.

BACKGROUND

Subcutaneous structures and blood vessels under skin are barely visible for naked eyes. In order to identify and locate the subcutaneous structures and blood vessels, medical doctors have to rely on the external outline of human body and their anatomic knowledge.

The blood vessels, including veins and arteries, are below the epidermis, and even covered by subcutaneous fat. Visible light imaging signals, reflected back from subcutaneous structures and blood vessels under the visible light illumination, are extremely faint and mixed with scattered light and various phantoms. Before puncturing, in order to make the blood vessels more visible, medical doctors often ask patients to clench their fists or flap the skin above the blood vessel. However, hindered by ages, or thickness of subcutaneous fat of patients etc., the visibility of subcutaneous blood vessels is still not satisfied in most cases. Injection relying on the vague images of blood vessels often results misalignment of the puncture, causing pain in patients, delaying optimal time for medical treatments, and even triggering injection incident.

In addition to drawing blood and injections in various occasions, blood vessels are also needed to be accurately located during acupuncture and medical surgeries.

An existing vein image enhancer, projects the obtained near-infrared (NIR) image of the venous blood vessels, by the visible light, directly onto the skin surface of a human body. In order to reduce the alignment errors, the existing vein image enhancer uses complex optical system, including complex mechanical servo mechanism, for ensuring the infrared imaging and the visible light projection being aligned in the same optical axis. Therefore, the design of the complex optical system will lead to enormous volume, heavy weight and huge power consumption, which is not suitable for mobile medical diagnosis and other portal applications.

SUMMARY

The primary purpose of the present disclosure is to provide an imaging device and a portable multispectral imaging and display apparatus. The multispectral imaging and display apparatus is able to overcome the drawbacks of the existing technology, and accurately detect and display the positions of the blood vessels, even in outdoor occasions, in a narrow space or powered by battery.

In one embodiment of the present disclosure, an imaging device is provided. The imaging device comprises a first image sensor disposed between a second image sensor and a lens module, and a center of the first image sensor and a center of the second image sensor are aligned on an optical axis of the lens module, wherein the first image sensor is configured to obtain image information of light radiation, came through the lens module, of a first spectral range.

The second image sensor is configured to obtain image information of light radiation, came through the first image sensor, of the second spectral range. The lens module is configured to focus the image information of the light radiation of the first spectral range on the first image sensor, and focus the image information of the light radiation of the second spectral range on the second image sensor.

In one embodiment of the present disclosure, a portable multispectral imaging and display apparatus is provided. The portable multispectral imaging and display apparatus comprises a main body, an imaging device disposed at one side of the main body, a plurality of light sources including at least one invisible light source, and a flat-panel display disposed at the other side of the main body.

The imaging device further comprises a first image sensor disposed between a second image sensor and a lens module, and a center of the first image sensor and a center of the second image sensor are aligned on an optical axis of the lens module, wherein the first image sensor is configured to obtain image information of light radiation, came through the lens module, of a first spectral range.

The second image sensor is configured to obtain image information of light radiation of the second spectral range.

The lens module is configured to focus the image information of the light radiation of the first spectral range on the first image sensor, and focus the image information of the light radiation of the second spectral range on the second image sensor.

The plurality of light sources include at least one invisible light source which emits an invisible light with the second spectral range, wherein the light sources are surrounded the imaging device.

The flat-panel display is configured to show the image information of the light radiation of the first spectral range and the image information of the light radiation of the second spectral range, wherein the image information of the light radiation of the first spectral range and the image information of the light radiation of the second spectral range are obtained and processed by the multispectral imaging and display apparatus.

In view of the above, the portable multispectral imaging and display apparatus of the present disclosure is capable of displaying the subcutaneous structures and blood vessels as two-dimensions, three-dimensions or even dynamic images directly and in real time, which greatly improves the visibility of subcutaneous blood vessels, and ensures direct and real-time observation by naked eyes, and accurately locates blood vessels, such that blood vessels will not be accidentally hurt or be treated separately.

BRIEF DESCRIPTION OF THE DRAWINGS

Embodiments of the present disclosure will now be described, by way of example only, with reference to the accompanying schematic drawings in which corresponding reference symbols indicate corresponding parts, and in which.

DETAILED DESCRIPTION

In the following, embodiments of the present disclosure will be described in detail referring to figures. The concept and its realizations of the present disclosure can be implemented in a plurality of forms, and should not be understood to be limited to the embodiments described hereafter. In contrary, these embodiments are provided to make the present disclosure more comprehensive and understandable, and so the conception of the embodiments can be conveyed to the technicians in the art fully. Same reference signs in the figures refer to same or similar structures, so repeated description of them will be omitted.

The features, structures or characteristics described can be combined in any appropriate way in one or more embodiments. In the description below, many specific details are provided to explain the embodiments of the present disclosure fully. However, the technicians in the art should realize that, without one or more of the specific details, or adopting other methods, components, materials etc., the technical proposal of the present disclosure can still be realized. In certain conditions, structures, materials or operations well known are not shown or described in detail so as not to obfuscate the present disclosure.

The technical contents of the present disclosure will be further described below with reference to the figures and embodiments.

It should be stated that a plurality of embodiments described below along with their combinations and varieties, beyond doubt are within the scope of the present disclosure.

Figure 1:
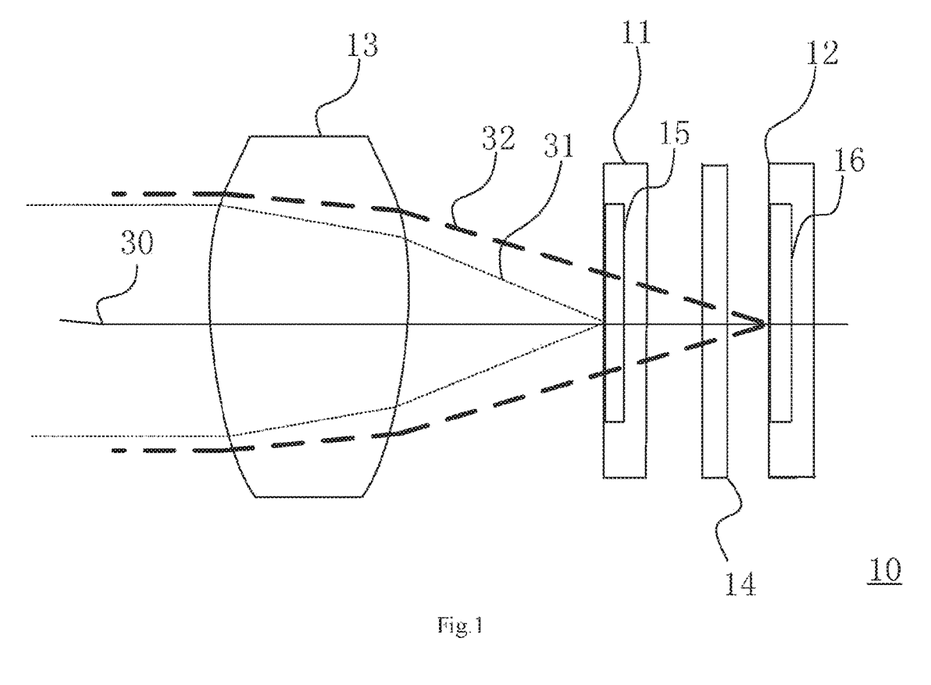
FIG. 1 shows a schematic diagram of an imaging device of one embodiment of the present disclosure.

FIG. 1 shows a schematic diagram of an imaging device of one embodiment of the present disclosure. In this embodiment, as shown in FIG. 1, the imaging device 10 includes a first image sensor 11, a second image sensor 12, a lens module 13 and a filter 14.

As shown in FIG. 1, the first image sensor 11 is disposed between the second image sensor 12 and the lens module 13, and a center of the first image sensor 11 and a center of the second image sensor 12 are aligned on an optical axis 30 of the lens module 13. The filter 14 is disposed between the first image sensor 11 and the second image sensor 12.

The first image sensor 11, in this embodiment, is configured to obtain image information of light radiation of a first spectral range, came through the lens module 13 and received by the pixel array 15 of the first image sensor 11. In this embodiment, the light radiation of the first spectral range is a visible light, which means the first image sensor 11 includes a visible light sensor responding to the visible light with a wavelength range of 400 nm to 760 nm. Moreover, in this embodiment, the type of silicon is selected in response to the wavelength range.

In some embodiments, the first image sensor 11 includes a photoelectric conversion module. The photoelectric conversion module includes a semiconductor thin film module. In some embodiments, the semiconductor thin film module includes a hydrogenated amorphous silicon. In some embodiments, the semiconductor thin film module includes an amorphous selenium, in some other embodiments, the semiconductor thin film module includes a metal oxide semiconductor.

The semiconductor thin film module is driven by at least one TFT (Thin Film Transistor). Moreover, the semiconductor thin film module and the at least one TFT are formed on an infrared transmitting substrate.

In some embodiments, the photoelectric conversion module includes a photodiode formed together with a complementary metal oxide semiconductor (CMOS) device on a crystalline silicon substrate. In some embodiments, the photoelectric conversion module is an electron potential well in a charge-coupled device (CCD) device. In some other embodiments, the photoelectric conversion module is a hydrogenated amorphous silicon photodiode film with a PIN structure formed on a glass substrate.

In this embodiment, the number of pixels of the pixel array 15 of the first image sensor 11 is in a range of half-size video graphics array (HVGA, 320×240) to full high definition (FHD, 1028×780). Moreover, in some embodiments, each pixel of the pixel array of the first image sensor 11 is respectively provided with a color filter (not shown) which allows the first image sensor 11 to obtain color images.

In one embodiment of the present disclosure, the first image sensor 11 is formed on a crystalline silicon substrate. The crystalline silicon substrate is then processed through the backside thinning process. The thickness of the processed crystalline silicon substrate does not affect the photoelectric conversion, and visible light images saving and obtaining. The effect of the backside thinning process is reducing the absorption loss of the infrared of the crystalline silicon substrate of the first image sensor 1, e.g. the visible light image sensor, and, in this embodiment, the thickness of the crystalline silicon substrate is less than 10 microns.

The second image sensor 12 is configured to obtain image information of a light radiation of a second spectral range, came through the first image sensor 11 and received by the pixel array 16 of the second image sensor 12. In one embodiment of the present disclosure, the light radiation of the second spectral range is infrared. Thus, the second image sensor 12 includes a CMOS or a CCD infrared image sensor formed on a crystalline silicon substrate.

In some embodiments, the second image sensor 12 includes a pixel array 16 in response to types of the infrared radiation. For example, in some embodiments, a photodiode formed on a crystalline silicon substrate is selected for near-infrared (NIR) radiation from 760 nm to 1100 nm. Therefore, charge saving circuits, signal amplifying and scanning circuits, and signal and noise processing circuits are formed on the crystalline silicon substrate.

In some embodiments, for mid-wave infrared (MWIR), the lead sulphide (PbS) is able to response a light radiation with a wavelength up to 3 µm. In some embodiments, the lead selenide (PbSe) is able to response a light radiation with a wavelength up to 5 µm. In some embodiments, a bolometer is used for infrared radiation with a wavelength up to 10 µm, e.g. thermal image. In these cases, charge saving circuits, amplifying and scanning circuits, and the signal and noise processing circuits can be relied on an integrated circuit (IC), or a MEMS device. The MEMS device includes energy conversion elements, e.g. photoelectric conversion modules, the circuits which are formed on a silicon substrate.

As shown in FIG. 1, in one embodiment of the present disclosure, the first image sensor 11, and the second image sensor 12 are aligned on the optical axis 30 of the lens module 13. Therefore, the optical module 13 of the imaging device 10 has compact size, and the visible light image 31 is aligned to the infrared image 32.

As shown in FIG. 1, in this embodiment, the lens module 13 is configured to focus the visible light 31 of an incident light onto the pixel array 15 of the first image sensor 11, and focus an infrared 32 on to the pixel array 16 of the second image sensor 12. The lens module 13, in this embodiment, is a visible light and infrared transmission lens module. Moreover, in some embodiments, the lens module 13 includes a lens. In some embodiments, the lens module 13 includes a plurality of lenses.

In one embodiment of the present disclosure, the imaging device 10 further comprises an optical filter 14 disposed between the first image sensor 11 and the second image sensor 12. The optical filter 14 is configured to filter out the visible light, unabsorbed by the first image sensor 11, to ensure the second image sensor 12 to absorb an optimized invisible light radiation, e.g. infrared radiation. Moreover, in some embodiments, if the visible light radiation is completely absorbed by the first image sensor 11, the optical filter 14 is omitted.

Furthermore, in one embodiment of the present disclosure, the imaging device 10 further includes a polarizer (not shown). The polarizer is disposed between the first image sensor 11 and the second image sensor 12. The polarizer is configured to filter out the scattered infrared to ensure the second image sensor 12 to receive optimized infrared.

Figure 2:
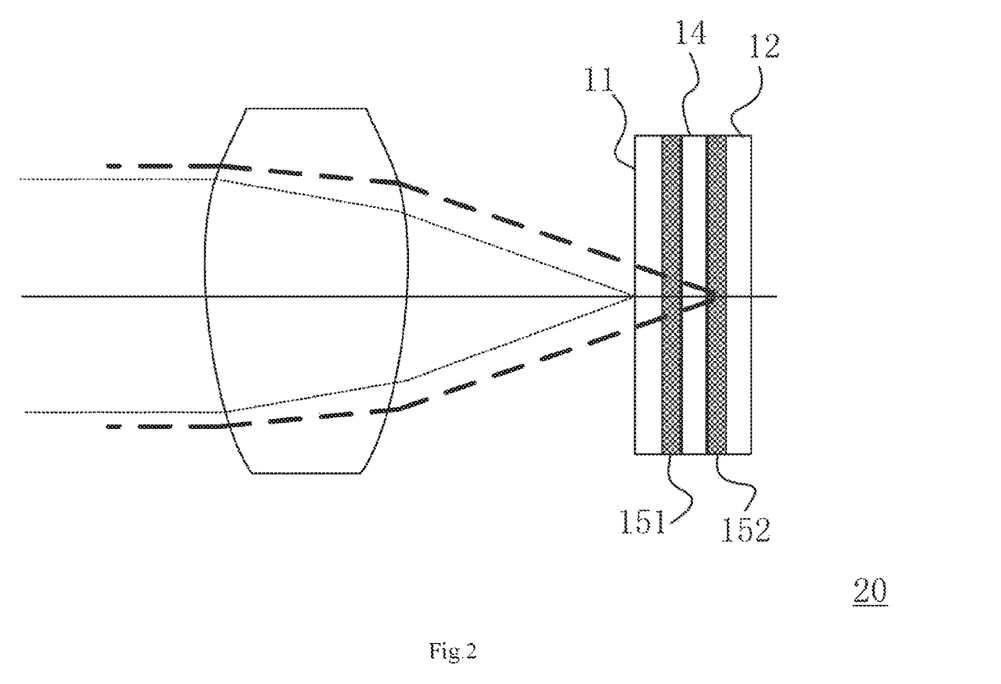
FIG. 2 shows a schematic diagram of an imaging device of one embodiment of the present disclosure.

FIG. 2 shows a schematic diagram of an imaging device of one embodiment of the present disclosure. The imaging device of FIG. 2 is similar to the imaging device of FIG. 1 but further includes a first optical adhesive 151 disposed between the first image sensor 11 and the optical filter 14, and a second optical adhesive 152 disposed between the optical filter 14 and the second image sensor 12. In this embodiment, the a first optical adhesive 151 is used to bond the first image sensor 11 to a side of the optical filter 14, and a second optical adhesive 152 is used to bond the second image sensor 12 to the other side of the optical filter 14.

Furthermore, in order to reduce multiple reflection and absorption of light radiation in the first optical adhesive 151, the first optical adhesive 151 is adequately made that its refractive index is approximately equal to a mean value of refractive index of the first image sensor 11 and the optical filter 14. Similar effort is made as well for the second optical adhesive 152 in order to minimize light loss inside of the adhesive.

In one embodiment of the present disclosure, the first image sensor 11 includes a hydrogenated amorphous silicon thin film formed on a glass substrate. Therefore, in this embodiment, a difference value of the infrared refractive index of the first optical adhesive 151, and an average refractive value of the filter 14 and a side, adjacent to the first optical adhesive 151, of the first image sensor 11 is less than or equal to 0.25. Moreover, in this embodiment, a difference value of the infrared refractive index of the second optical adhesive 152, and an average refractive value of the filter 14 and a side of the second image sensor 12 adjacent to the first optical adhesive 152 is less than or equal to 0.25.

Figure 3:
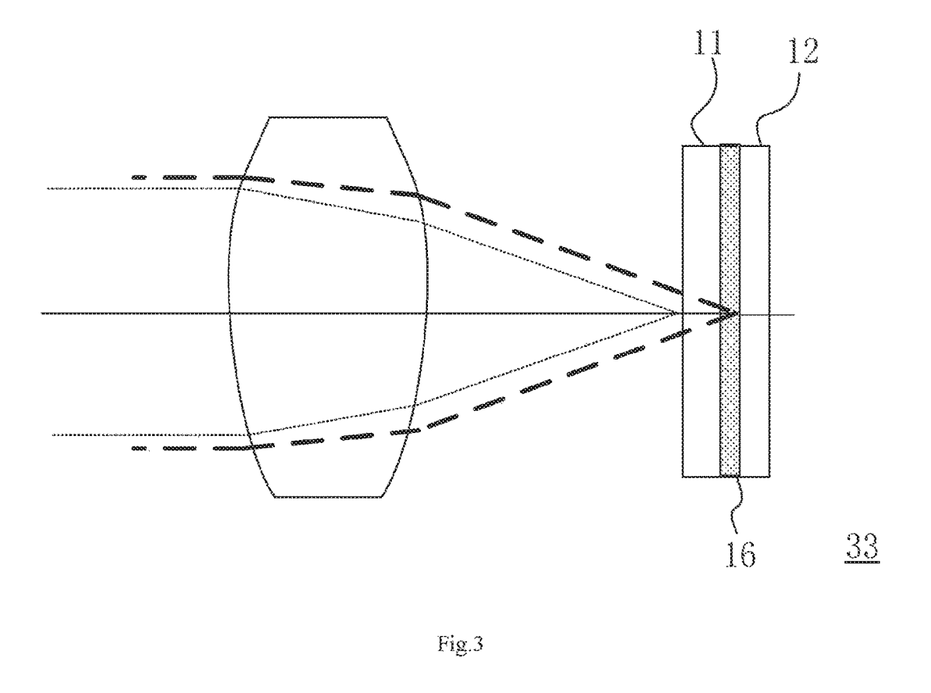
FIG. 3 shows a schematic diagram of an imaging device of one embodiment of the present disclosure.
Figure 4:
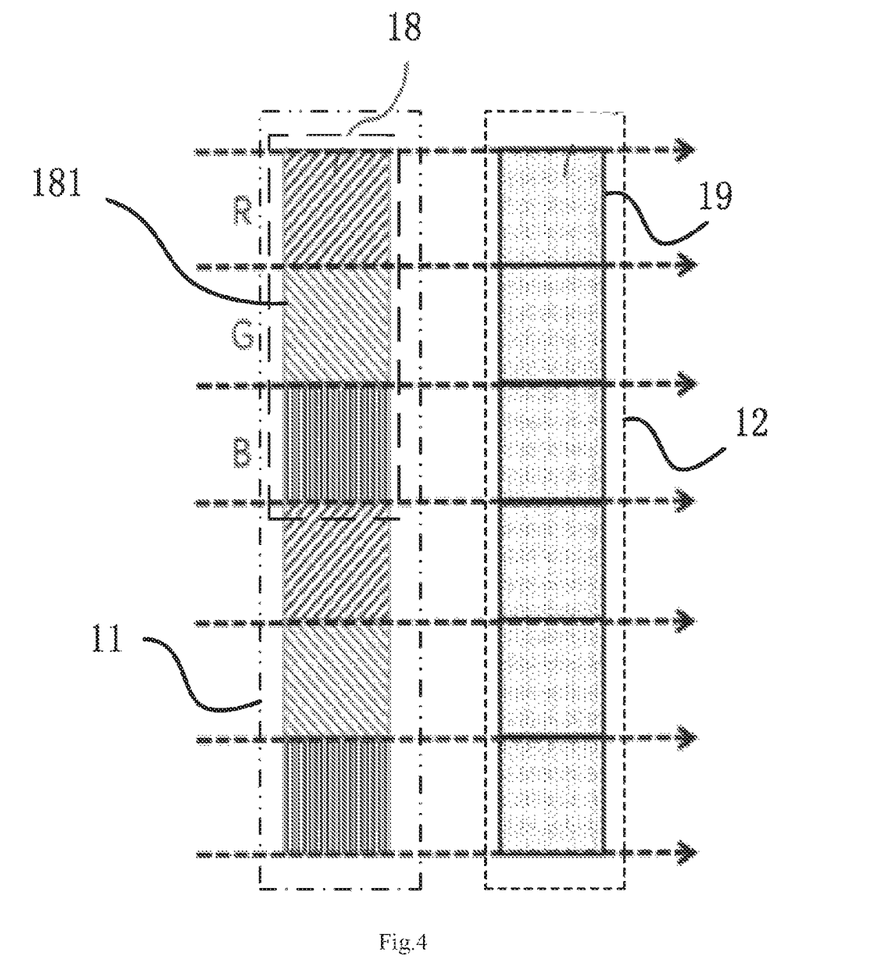
FIG. 4 shows a schematic diagram of an alignment of a plurality of visible light image detection pixel units of a first image sensor and a plurality of infrared image detection pixel units of a second image sensor of an imaging device of one embodiment of the present disclosure.
Figure 5:
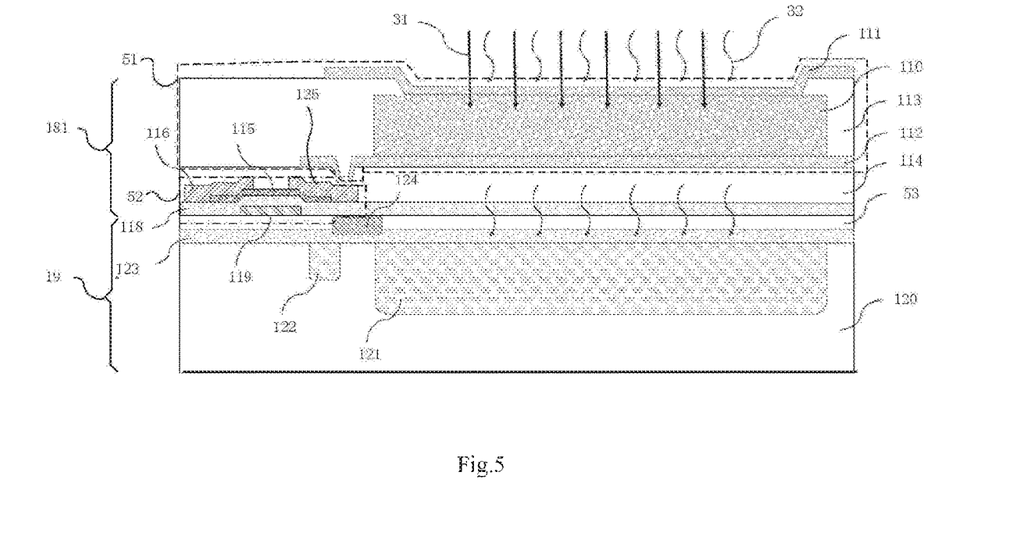
FIG. 5 shows a schematic diagram of the visible light image detection pixel and the infrared image detection unit of FIG. 4 of an imaging device of one embodiment of the present disclosure.

FIG. 3 to FIG. 5 show embodiments of an imaging device of the present disclosure. FIG. 3 shows a schematic diagram of an imaging device of one embodiment of the present disclosure. As shown in FIG. 3, the imaging device 30 in FIG. 3 is similar to the imaging device in FIG. 1 but includes an insulating region 16 disposed between the first image sensor 11 (e.g. an amorphous silicon thin film module) and the second image sensor 12 (e.g. a CMOS infrared image sensor or a CCD infrared image sensor). The insulating region 16 is configured to reduce parasitic capacitance caused by capacitive coupling between the first image sensor 11 and the second image sensor 12. Furthermore, the signal crosstalk and increments of the switching noise (e.g. KTC noise) caused by the parasitic capacitance are reduced as well.

FIG. 4 shows a schematic diagram of an alignment of a plurality of visible light image detection pixel units of a first image sensor and a plurality of infrared image detection pixel units of a second image sensor of an imaging device of one embodiment of the present disclosure. In this embodiment, as shown in FIG. 4, the first image sensor 11 includes a plurality of visible light image detection pixel units 18 and each of the visible light image detection pixel units 18 includes a plurality of visible light image detection pixel 181. The second image sensor 12 includes a plurality of infrared image detection pixel units 19.

As shown in FIG. 4, in this embodiment, each of the visible light image detection pixel units 18 includes three visible image detection pixels 181, which is respectively a red pixel, a green pixel and a blue pixel. In this embodiment, each of the infrared image detection pixel units 19 is arranged in response to a visible light image detection pixel 181. Moreover, in this embodiment, in order to reduce Moire strip caused on an infrared image of the infrared image detection unit 19, the infrared image detection unit 19 is aligned to the visible light image detection pixel 181.

FIG. 5 shows a schematic diagram of the visible light image detection pixel and the infrared image detection unit of FIG. 4 of an imaging device of one embodiment of the present disclosure. AS shown in FIG. 5, a first insulation region 53 is disposed between the visible light image detection pixel 181 and the infrared image detection unit 19.

In this embodiment, the visible light detection pixel 181 includes a photodiode 51, an amorphous silicon TFT 52. The photodiode 51 is configured to be a visible light photoelectric conversion module, e.g. a a-Si:H PIN photodiode. The amorphous silicon TFT 52 is configured to be a switch.

The photodiode 51 includes a first transparent conductive film 111, a second transparent conductive film 112, a p-type heavily doped region (not shown), an n-type heavily doped region (not shown) an intrinsic semiconductor region 110 and an insulation region 113. As shown in FIG. 5, the intrinsic semiconductor region 110 is disposed between the first transparent conductive region 111 and the second transparent conduct region 112. The intrinsic semiconductor region 110 is respectively and electrically coupled to the first transparent conductive region 111 and the second transparent conduct region 112.

The first transparent conductive region 111 and the second transparent conductive region 112 apply a reverse bias voltage on the intrinsic semiconductor region 110. In some embodiments, an effective band gap of the intrinsic semiconductor region 110 is in a range of 1.6 eV to 2.1 eV, and the thickness of the intrinsic semiconductor region 110 is in a range of 1.0 μm to 2.2 μm. The reverse bias voltage is in a range of −5 V to −10 V.

Though the intrinsic semiconductor region 110 is capable of converting the visible light to electron-hole pairs, for the near infrared light having wavelength in a range of 760 nm to 1000 nm, the intrinsic semiconductor 110 with effective band gap greater than 1.6 eV, will not absorb most of the near infrared light and therefore acts as almost transparent to the near infrared light.

In this embodiment, when the amorphous silicon TFT 52 is conducted, an external amplifier (not shown), electrically coupled to the amorphous silicon TFT 52, is configured to amplify electrical signal, came from the second transparent conduct region 112.

In this embodiment, the amorphous silicon TFT 52 includes a bottom-gate TFT. As shown in FIG. 5, the amorphous silicon TFT 52 further includes an amorphous silicon channel 115, a source electrode 116, a drain electrode 125 coupled to the second transparent conductive region 112 of the photodiode 51, a gate insulating region 118, and a control gate electrode 119. In this embodiment, the source electrode 116 and the drain electrode 125 are respectively formed by a conductive metal. Moreover, a second insulation region 114 is disposed between the photodiode 51 and the amorphous silicon TFT 52, and servers as a passivation for TFT 52. In some embodiments, the control gate electrode 119 includes a metal thin film. In some embodiments, the control gate electrode 119 includes a polycrystalline silicon thin film.

As shown in FIG. 5, the infrared image detection pixel unit 19 includes a crystalline silicon substrate 120, a photoelectric conversion and charge saving region 121, a charge transmission region 122, a third insulating region 123, and a transmission gate electrode 124. As shown in FIG. 5, the photoelectric conversion and charge saving region 121 is disposed in the crystalline silicon substrate 120. The charge transmission region 122 is disposed in the crystalline silicon substrate 120, and under the amorphous silicon TFT 52. The third insulation region 123 is formed on the crystalline silicon substrate 120, the photoelectric conversion and charge saving region 121 and the charge transmission region 122.

Furthermore, as shown in FIG. 5, when the thickness of intrinsic semiconductor region 110 of the hydrogenated amorphous silicon thin film of the photodiode 51 is thicker than 1.5 μm, the visible light 31 is about completely absorbed by the photodiode 51. The infrared 32, having a wavelength greater than 760 nm, goes through the visible light detection pixel 181 and reaches the photoelectric conversion and charge saving region 121 of the infrared image detection unit 19, since the effective band gap of the intrinsic semiconductor region 110 of the hydrogenated amorphous silicon thin film of the photodiode 51 is greater than 1.6 eV. The infrared absorbed by the hydrogenated amorphous silicon thin film of the photodiode 51 is then converted to electron hole pairs and ionized by an electric field. The ionized charges are then saved in the photoelectric conversion and charge saving region 121.

In this embodiment, when a turn-on voltage is applied on the control gate electrode 119 of the amorphous silicon TFT 52, the charges saved in the photodiode 51 are transmitted to an external preamplifier for further signal process. Moreover, the charges saved in the photoelectric conversion and charge saving region 121 are transmitted to external circuits for further signal process after the amorphous silicon channel 115 is conducted by the transmission gate electrode 124.

In the embodiments shown in FIG. 3 to FIG. 5, since the infrared image detection pixel units 19 only detect monochrome images, the spatial resolution of a direction of the second image sensor 12 is three times to the spatial resolution of the first image sensor 11. Therefore, in order to enhance the resolution of the infrared image and reduce Moire fringe caused on an infrared image, an infrared image detection pixel unit 19 is arranged in response to a visible light image detection unit 18 including a plurality of visible light image detection pixels 181.

Figure 6:
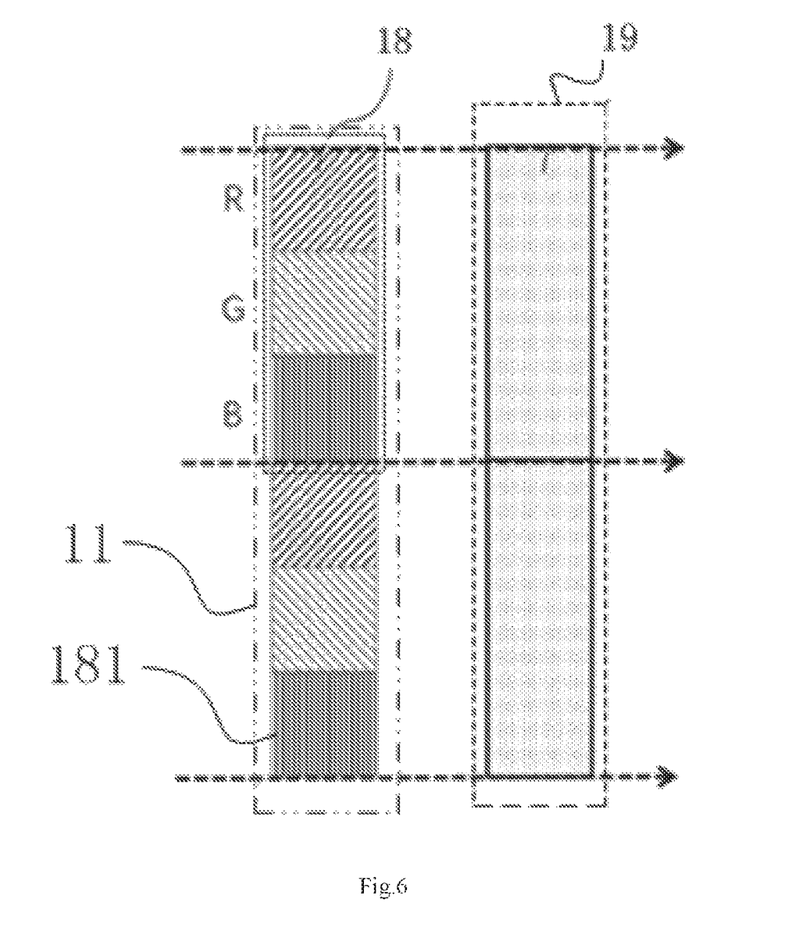
FIG. 6 shows a schematic diagram of an alignment of a visible light image detection pixel unit of a first image sensor and an infrared image detection pixel unit of a second image sensor of an imaging device of one embodiment of the present disclosure.

FIG. 6 shows a schematic diagram of an alignment of a visible light image detection pixel unit of a first image sensor and an infrared image detection pixel unit of a second image sensor of an imaging device of one embodiment of the present disclosure. In this embodiment, as shown in FIG. 6, the imaging device of FIG. 6 is similar to the imaging device of FIG. 4, but an infrared image detection unit 19 of the second image sensor 12 is arranged in response to a visible light image detection pixel unit 18 of the first image sensor 11 in the imaging device 60 of FIG. 6. In this embodiment, the visible light image detection pixel unit 18 includes three visible image detection pixels 181, which is respectively a red pixel, a green pixel and a blue pixel.

Figure 7:
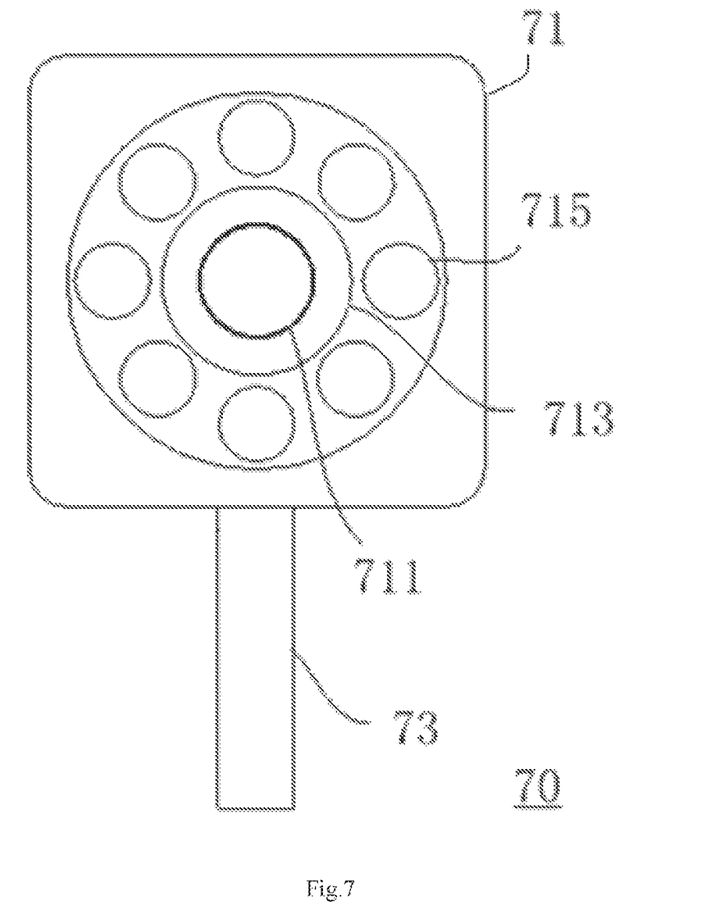
FIG. 7 shows a schematic diagram of a portable multispectral imaging and display apparatus of one embodiment of the present disclosure.
Figure 8:
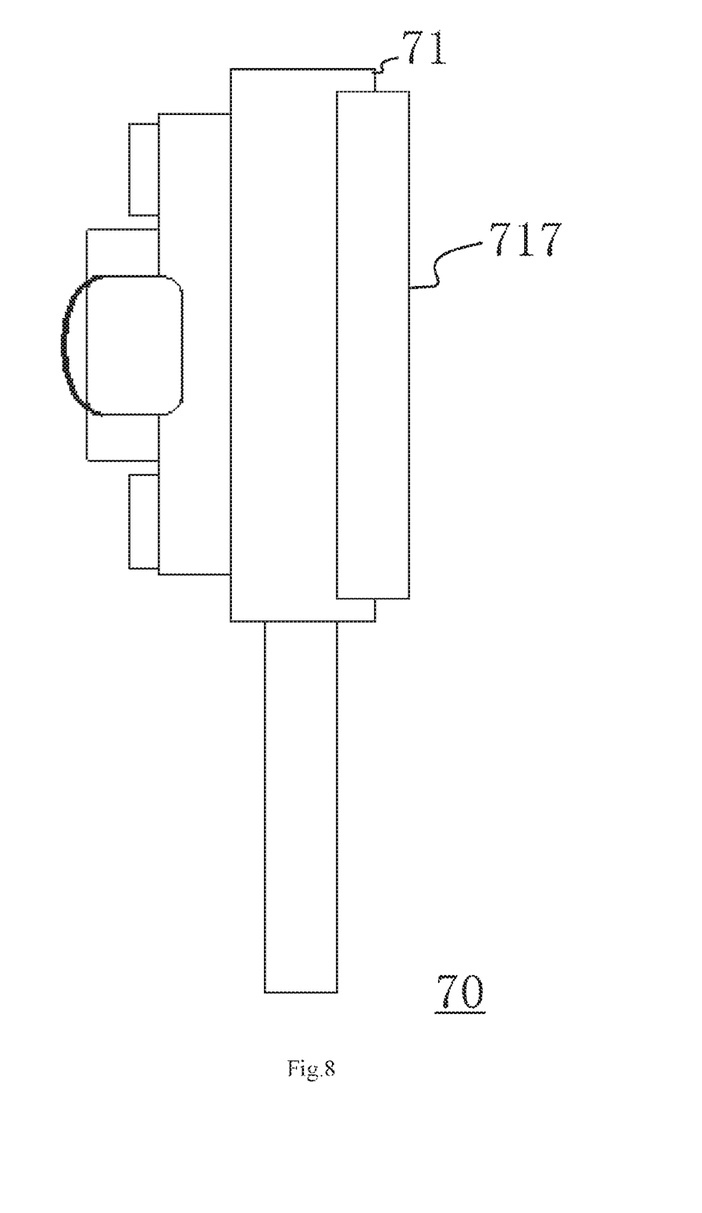
FIG. 8 shows a cross-sectional view of the portable multispectral imaging and display apparatus of FIG. 7.

FIG. 7 shows a schematic diagram of a portable multispectral imaging and display apparatus of one embodiment of the present disclosure. FIG. 8 shows a crossentional view of the portable multispectral imaging and display apparatus in FIG. 7. As shown in FIG. 7, the portable multispectral imaging and display apparatus 70 includes a main body 71 coupled to a handler 73. A first side of the main body 71 further includes a imaging device 711, a light-absorbing plateau 713, a plurality of light sources 715 including at least one invisible light source. In this embodiment, the at least one invisible light source includes an infrared light source and the rest of the light sources are visible light sources. Moreover, as shown in FIG. 8, a second side of the main body 71 further includes a flat-panel display screen 717, wherein, in this embodiment, the second side is arranged opposite to the first side. In this embodiment, the handler 73 includes a operating mechanism, which allow users to operate the portable multispectral imaging and display apparatus 70.

As shown in FIG. 7, the light-absorbing plateau 713 is disposed between the imaging device 711 and the light sources 715 surrounded the imaging device 711. In this embodiment, the outer surface of the light-absorbing plateau 713 are coated with light-absorbing materials. Moreover, the light-absorbing plateau 713 further includes a step structure or a wall structure, which blocks direct light paths between the light sources 715 and the imaging device 711 and will improve the image quality including contrast and brightness.

Figure 9:
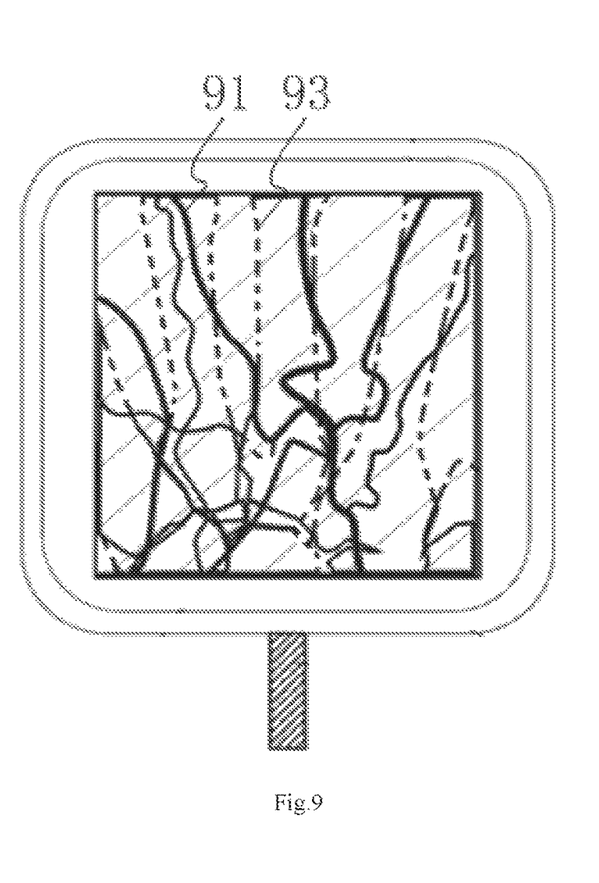
FIG. 9 shows a schematic diagram of the portable multispectral imaging and display apparatus displaying an infrared image and an X-ray image of one embodiment of the present disclosure.

FIG. 9 shows a schematic diagram of the portable multispectral imaging and display apparatus displaying an infrared image and an X-ray image of one embodiment of the present disclosure. In some embodiments, as shown in FIG. 9, the infrared image 91 is a pre-saved image of an object, in this embodiment, the infrared image 91, e.g. a blood vessel image, is a real time image of the object. The X-ray image 93, e.g. a bone image, is a pre-saved image of the object. Therefore, in this embodiment, during medical examining, the locations of blood vessels and bones can be identified.

The absorption rate of infrared, e.g. near infrared (NIR) with a wavelength in a range of 760 nm to 1000 nm, of hemoglobin (HGB) in blood vessels is different from that of other tissues. Therefore, after an infrared image of the blood vessels is firstly captured and proceeded with image process, the processed infrared image of the vessels is stacked with a visible light image of the portion covered the vessels and shown on a display, which allow the vessels to be identified accurately. Moreover, in some embodiments, information or other images, e.g. translucent images, relevant to the vessels are shown on the display as well.

In summary, the portable multispectral imaging and display device of the present disclosure captures the relevant information of subcutaneous structures and blood vessels, which are shown as an image or a video stream. Therefore, the visibility of subcutaneous structures and blood vessels are identified and located accurately.

What is claimed is:

1. An imaging device, comprising:
   a first image sensor disposed between a second image sensor and a lens module, and a center of the first image sensor and a center of the second image sensor are aligned on an optical axis of the lens module, wherein the first image sensor is configured to obtain image information of light radiation, passing through the lens module, of a first spectral range;
   wherein the second image sensor is configured to obtain image information of the light radiation, passing through the first image sensor, of the second spectral range; and
   wherein the lens module is configured to focus the image information of the light radiation of the first spectral range on the first image sensor, and focus the image information of the light radiation of the second spectral range on the second image sensor.

2. The imaging device of claim 1 further comprising an optical filter disposed between the first image sensor and the second image sensor, wherein the optical filter is configured to filter out the light radiation of the first spectral range.

3. The imaging device of claim 2, wherein a first optical adhesive is used to bond the first image sensor to one side of the optical filter, and a second optical adhesive is used to bond the second image sensor to the other side of the optical filter.

4. The imaging device of claim 3, wherein a difference value of an infrared refractive index of the first optical adhesive, and an average infrared refractive index of the optical filter and a surface contact to the first optical adhesive, of the first image sensor is less than equal to 0.25.

5. The imaging device of claim 3, wherein a difference value of an infrared refractive index of the second optical adhesive, and an average infrared refractive index of the optical filter and a surface contact to the second optical adhesive, of the second image sensor is less than or equal to 0.25.

6. The imaging device of claim 1 further comprising a polarizer, wherein the polarizer is disposed between the first image sensor and the second image sensor.

7. The imaging device of claim 1, wherein the light radiation of the first spectral range includes visible light with a wavelength range of 0.4 microns to 0.76 microns, and the light radiation of the second spectral range includes infrared with a wavelength range of 0.76 microns to 10 microns.

8. The imaging device of claim 1, wherein the first image sensor is formed on a silicon substrate, processed by backside thinning process, wherein an average thickness of the silicon substrate is less than 10 microns.

9. The imaging device of claim 1, wherein the first image sensor comprises a photoelectric conversion module, and the photoelectric conversion module includes a semiconductor thin film module, wherein the semiconductor thin film module includes a hydrogenated amorphous silicon, an amorphous selenium or an metal oxide semiconductor, wherein the second image sensor includes a complementary metal oxide semiconductor (CMOS) or charge coupled device (CCD) infrared image sensor formed on a crystalline silicon substrate.

10. The imaging device of claim 9, wherein the semiconductor thin film module is driven by at least one TFT, and the semiconductor thin film module and at least one TFT are formed on an infrared transmission substrate.

11. The imaging device of claim 9, wherein the semiconductor thin film module is driven by the TFT array and the semiconductor thin film module is formed on an insulating film, wherein the insulating film is formed on the second image sensor.

12. The imaging device of claim 9, wherein the semiconductor thin film module is formed on the second image sensor, wherein a selection switch, a signal amplifying circuit, a noise reduction circuit, which control image signals of the semiconductor thin film module, and the second image sensor are formed on the crystalline silicon substrate.

13. The imaging device of claim 1, wherein the first image sensor comprises a first pixel array and the second image sensor comprises a second pixel array, wherein each pixel of the second pixel array is aligned in a manner to receive light of the second spectral range passing through at least one pixel of the first pixel array.

14. A portable multispectral imaging and display apparatus, comprising:
   a main body;
   an imaging device, disposed at one side of the main body, further comprising:
      a first image sensor disposed between a second image sensor and a lens module, and a center of the first image sensor and a center of the second image sensor are aligned on an optical axis of the lens module, wherein the first image sensor is configured to obtain image information of light radiation, came through the lens module, of a first spectral range;
      wherein the second image sensor is configured to obtain image information of light radiation, came through the first image sensor, of the second spectral range in response to the light radiation of the second spectral range; and
      wherein the lens module is configured to focus the image information of the light radiation of the first spectral range on the first image sensor, and focus the image information of the light radiation of the second spectral range on the second image sensor;
   a plurality of light sources including at least one invisible light source which emits an invisible light with the second spectral range, wherein the light sources are surrounded the imaging device; and
   a flat-panel display, disposed at the other side of the main body, configured to show the image information of the light radiation of the first spectral range and the image information of the light radiation of the second spectral range, wherein the image information of the light radiation of the first spectral range and the image information of the light radiation of the second spectral range are obtained and processed by the multispectral imaging and display apparatus.

15. The portable multispectral imaging and display apparatus of claim 14, wherein the imaging device further comprises an optical filter, wherein the optical filter is disposed between the first image sensor and the second image sensor, and the optical filter is configured to block the light radiation of the first spectral range.

16. The portable multispectral imaging and display apparatus of claim 14, wherein the imaging device further comprises a polarizer, and the polarizer is disposed between the first image sensor and the second image sensor.

17. The portable multispectral imaging and display apparatus of claim 14, wherein the light radiation of the first spectral range is visible light including a wavelength range of 0.4 microns to 0.76 microns, and the light radiation of the second spectral range includes infrared including a wavelength range of 0.76 microns to 10 microns.

\* \* \* \* \*